United States Patent
Sato et al.

(10) Patent No.: US 10,967,157 B2
(45) Date of Patent: Apr. 6, 2021

(54) BALLOON CATHETER

(71) Applicant: KANEKA CORPORATION, Osaka (JP)

(72) Inventors: Masao Sato, Osaka (JP); Soichiro Kita, Osaka (JP); Hitoshi Tahara, Osaka (JP); Ryoji Nakano, Osaka (JP); Motokazu Watanabe, Osaka (JP); Takuji Nishide, Osaka (JP)

(73) Assignee: KANEKA CORPORATION, Osaka (JP)

( * ) Notice: Subject to any disclaimer, the term of this patent is extended or adjusted under 35 U.S.C. 154(b) by 190 days.

(21) Appl. No.: 16/240,204

(22) Filed: Jan. 4, 2019

(65) Prior Publication Data

US 2019/0134360 A1    May 9, 2019

Related U.S. Application Data

(63) Continuation of application No. PCT/JP2017/023960, filed on Jun. 29, 2017.

(30) Foreign Application Priority Data

Jul. 4, 2016    (JP) .............. JP2016-132844

(51) Int. Cl.
*A61M 25/10* (2013.01)
*A61L 29/16* (2006.01)
(Continued)

(52) U.S. Cl.
CPC ........... *A61M 25/104* (2013.01); *A61L 29/16* (2013.01); *A61M 25/1002* (2013.01);
(Continued)

(58) Field of Classification Search
CPC .............................. A61B 17/12136
See application file for complete search history.

(56) References Cited

U.S. PATENT DOCUMENTS

| 5,102,402 A | 4/1992 | Dror et al. |
| 5,304,121 A | 4/1994 | Sahatjian |

(Continued)

FOREIGN PATENT DOCUMENTS

| JP | H05505132 A | 8/1993 |
| JP | 2002539888 A | 11/2002 |

(Continued)

OTHER PUBLICATIONS

International Search Report issued in International Application No. PCT/JP2017/023960; dated Aug. 8, 2017 (2 pages).

(Continued)

*Primary Examiner* — Theodore J Stigell
*Assistant Examiner* — Rachel T. Smith
(74) *Attorney, Agent, or Firm* — Osha Bergman Watanabe & Burton LLP

(57) ABSTRACT

A balloon catheter includes a shaft, and a balloon provided outside the shaft. A drug is provided on an outer surface of the balloon, and the balloon has at least a straight tube part. A change ratio of an outer diameter of the straight tube part, (D28−D24)/D24, is 1.1% or less. D24 is the outer diameter of the straight tube part when an internal pressure of 2.43 MPa (24 atm) is applied, and D28 is the outer diameter of the straight tube part when an internal pressure of 2.84 MPa (28 atm) is applied.

14 Claims, 5 Drawing Sheets

(51) Int. Cl.
*A61L 29/08* (2006.01)
*B29L 31/00* (2006.01)

(52) U.S. Cl.
CPC ........ *A61M 25/1029* (2013.01); *A61L 29/085* (2013.01); *A61L 2300/606* (2013.01); *A61M 25/1038* (2013.01); *A61M 2025/1004* (2013.01); *A61M 2025/105* (2013.01); *A61M 2025/109* (2013.01); *A61M 2025/1031* (2013.01); *A61M 2025/1068* (2013.01); *A61M 2025/1075* (2013.01); *A61M 2025/1084* (2013.01); *A61M 2025/1088* (2013.01); *B29L 2031/7543* (2013.01)

(56) References Cited

U.S. PATENT DOCUMENTS

| | | | |
|---|---|---|---|
| 5,324,261 | A | 6/1994 | Amundson et al. |
| 5,348,538 | A * | 9/1994 | Wang ................ A61M 25/1029 604/103.12 |
| 5,370,614 | A | 12/1994 | Amundson et al. |
| 5,893,840 | A | 4/1999 | Hull et al. |
| 6,258,099 | B1 | 7/2001 | Mareiro et al. |
| 2001/0039395 | A1 | 11/2001 | Mareiro et al. |
| 2003/0114915 | A1 | 6/2003 | Mareiro et al. |
| 2006/0182873 | A1 | 8/2006 | Klisch et al. |
| 2007/0225800 | A1 | 9/2007 | Sahatjian et al. |
| 2008/0033477 | A1 | 2/2008 | Campbell et al. |
| 2009/0038752 | A1 | 2/2009 | Weng et al. |
| 2009/0306582 | A1 | 12/2009 | Granada et al. |
| 2010/0076401 | A1 | 3/2010 | Von Oepen et al. |
| 2013/0023817 | A1 | 1/2013 | Speck et al. |
| 2013/0046231 | A1 | 2/2013 | Speck et al. |
| 2013/0338572 | A1 | 12/2013 | Speck et al. |
| 2014/0128801 | A1 | 5/2014 | Speck et al. |
| 2014/0188036 | A1 | 7/2014 | Speck et al. |
| 2015/0297797 | A1 | 10/2015 | Speck et al. |
| 2016/0095960 | A1 | 4/2016 | Speck et al. |
| 2017/0340778 | A1 | 11/2017 | Speck et al. |
| 2018/0104383 | A1 * | 4/2018 | Wang ..................... A61P 37/06 |

FOREIGN PATENT DOCUMENTS

| | | |
|---|---|---|
| JP | 2008529740 A | 8/2008 |
| JP | 2008534032 A | 8/2008 |
| JP | 2009207533 A | 9/2009 |
| JP | 2009531157 A | 9/2009 |
| JP | 2009254626 A | 11/2009 |
| JP | 2010500104 A | 1/2010 |
| JP | 2011529350 A | 12/2011 |
| JP | 2013523209 A | 6/2013 |
| JP | 2013524900 A | 6/2013 |
| JP | 2014198134 A | 10/2014 |
| JP | 2015217260 A | 12/2015 |
| WO | 2011119159 A1 | 9/2011 |

OTHER PUBLICATIONS

Written Opinion of the International Searching Authority issued in International Application No. PCT/JP2017/023960; dated Aug. 8, 2017 (5 pages).

* cited by examiner

19 17    18

19 17    18

19 17    18

19 17 18

19 17 18

17 18 17
(17A) (17B)

17 18 17
(17A) (17B)

BALLOON CATHETER

TECHNICAL FIELD

One or more embodiments of the present invention relate to a balloon catheter, and in particular, it relates to a balloon catheter provided with a drug.

BACKGROUND

It is known that various diseases occur when a stenosis occurs in a blood vessel which is a flow path for blood circulation in a body and blood circulation is disrupted. In particular, when a stenosis occurs in a coronary artery which supplies blood to a heart, there is a risk that serious diseases such as angina and myocardial infarction may result. As a method of treating such a stenosis part of a blood vessel, angioplasty in which a stenosis is expanded using a balloon catheter (e.g., PTA, PTCA) is known. Angioplasty is widely performed because it is a minimally invasive therapy that does not require thoracotomy such as a bypass surgery.

In the case of angioplasty, restenosis may occur in the stenosis part which was expanded, and as a treatment to reduce a frequency of occurring such restenosis (namely, a restenosis rate), a treatment using a drug-eluting stent which has a drug layer on its surface has been performed. Also, a drug-eluting balloon catheter in which a drug is held on a balloon of a balloon catheter has been proposed (for example, Patent Literatures 1 to 4). As using the drug-eluting balloon catheter, it is possible to transfer a drug to a blood vessel wall by expanding the balloon at a stenosis part or a lesion part, and it is expected to suppress occurrence of restenosis. Advantages of the treatment using the drug-eluting balloon catheter include that a foreign object is not left in a body, and small blood vessels into which a stent can not be inserted can also be treated.

CITATION LIST

Patent Literature

Patent Literature 1
U.S. Pat. No. 5,304,121
Patent Literature 2
Japanese Unexamined Laid-open Patent Application Publication No. H05-505132
Patent Literature 3
Japanese Unexamined Laid-open Patent Application Publication No. 2008-529740
Patent Literature 4
Japanese Unexamined Laid-open Patent Application Publication No. 2015-217260

Though there is a case that a hardened stenosis part due to calcification or the like is formed on an inner wall of a blood vessel, a drug-eluting balloon catheter targeting such a hardened stenosis or lesion part is little known. One or more embodiments of the present invention have been made in view of the above circumstances, and provide a balloon catheter which can effectively deliver a drug to a hardened stenosis or lesion part due to calcification or the like.

For suppressing an occurrence of restenosis by applying a drug to a hardened stenosis or lesion part, it is effective to expand the stenosis or lesion part by a balloon and then to deliver a drug deeply into the stenosis or lesion part. In order to expand such a hardened stenosis or lesion part by a balloon and deliver a drug deeply into it, the balloon needs to be pressurized with a relatively high expansion pressure.

However, as a result of studies by the present inventors, it has been cleared that: on expanding such a hardened stenosis or lesion part and applying a drug thereto, there is a case that a hardened stenosis or lesion part could not be expanded to deliver a drug deeply into it only by pressurizing a balloon at an expansion pressure of 20 atm, for example; and for surely exerting the effect by a drug-eluting balloon catheter on the hardened stenosis or lesion part, it is effective to pressurize a balloon at a more higher expansion pressure such as 24 atm to 28 atm without expanding the balloon in the radial direction as much as possible and to apply the drug.

SUMMARY

One or more embodiments of the present invention relate to a balloon catheter comprising a shaft and a balloon provided on an outside of the shaft, wherein a drug is provided on an outer surface of the balloon, the balloon has at least a straight tube part, and a change ratio of an outer diameter of the straight tube part, (D28−D24)/D24, is 1.1% or less, provided that the outer diameter of the straight tube part when pressurized at 2.43 MPa (24 atm) is D24 and the outer diameter of the straight tube part when pressurized at 2.84 MPa (28 atm) is D28.

In one or more embodiments, the balloon is preferably formed such that a change ratio of a length of the straight tube part in the axial direction, (L28−L24)/L24, is 0.7% or less, provided that the length of the straight tube part in the axial direction when pressurized at 2.43 MPa (24 atm) is L24 and the length of the straight tube part in the axial direction when pressurized at 2.84 MPa (28 atm) is L28. In one or more embodiments, the balloon is also preferably formed such that the change ratio of the length of the straight tube part in the axial direction, (L28−L24)/L24, is smaller than the change ratio of the outer diameter of the straight tube part, (D28−D24)/D24.

In one or more embodiments, it is preferable that the balloon comprises a base balloon and a reinforcement part provided on an outer surface of the base balloon in a linear pattern or a net-like pattern and formed to protrude on the outer surface of the balloon, and the drug is provided on the reinforcement part. In one or more embodiments, it is preferable that the reinforcement part has a height of 0.2 mm or more and 0.5 mm or less. In one or more embodiments, it is preferable that the reinforcement part protrudes outward in the radial direction of the balloon relative to a part other than the reinforcement part on the outer surface of the balloon when pressurized at 2.63 MPa (26 atm).

In one or more embodiments, it is also preferable that the balloon comprises a base balloon and a reinforcement part provided on an outer surface of the base balloon in a linear pattern of a net-like pattern and formed to protrude on the outer surface of the balloon, and the drug is provided on a part other than the reinforcement part on the outer surface of the balloon. In one or more embodiments, it is preferable that the reinforcement part has a height of 0.1 mm or more and 0.5 mm or less. In one or more embodiments, it is preferable that the part other than the reinforcement part on the outer surface of the balloon is formed to bulge outward in a radial direction of the balloon when pressurized at 2.63 MPa (26 atm).

In one or more embodiments, it is preferable that at least a part of the reinforcement part is provided so as to extend in the axial direction of the balloon. In one or more embodiments, it is preferable that the reinforcement part is formed by bonding a fiber material to the outer surface of the base balloon. In one or more embodiments, it is preferable that the drug is an antiproliferative agent or an immunosuppressive agent.

In the balloon catheter according to one or more embodiments of the present invention, since a drug is provided on the outer surface of the balloon and the outer diameter of the balloon is substantially constant in the expansion pressure range of as relatively high as 24 atm to 28 atm, the balloon can effectively expand a hard stenosis or lesion part when the balloon is pressurized at such a pressure range. Therefore, by disposing a drug on the outer surface of the thus formed balloon, the drug can be delivered deeply into a hard stenosis or lesion part to which a drug is usually hard to be delivered.

DETAILED DESCRIPTION OF EMBODIMENTS

Figure 1:
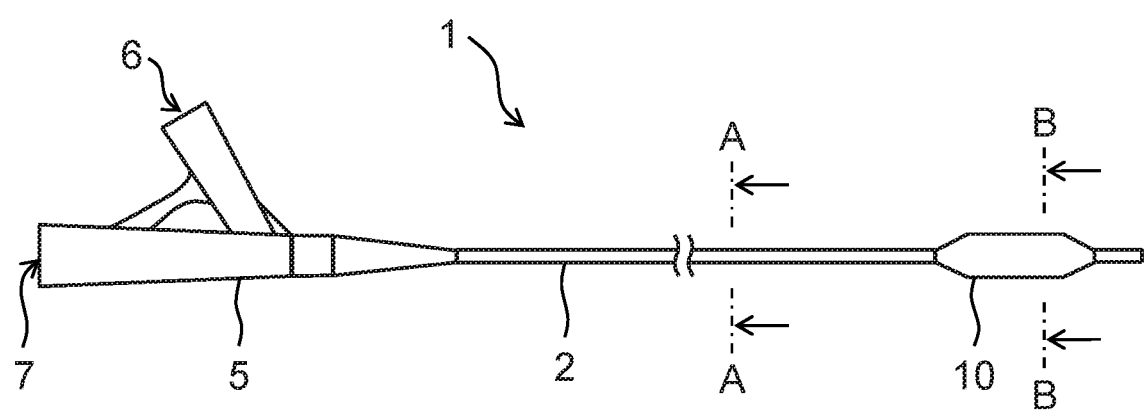
FIG. 1 shows an example of a plan view of a balloon catheter.

One or more embodiments of the present invention relate to a balloon catheter in which a drug is provided on an outer surface of a balloon, and in detail, it relates to a balloon catheter in which a drug is provided on an outer surface of a balloon, the balloon is formed so as to have a desired outer diameter at a relatively high expansion pressure of 24 atm to 28 atm, and expansion of the balloon in the radial direction is suppressed in such a pressure range. According to one or more embodiments of the balloon catheter, since the balloon can effectively expand a hard stenosis or lesion part, it is possible to deliver a drug deeply into the hard stenosis or lesion part to which a drug is usually hard to be delivered.

Hereinafter, one or more embodiments of the present invention will be specifically explained below based on the following embodiments; however, the present invention is not restricted by the embodiments described below of course, and can be certainly put into practice after appropriate modifications within in a range meeting the gist of the above and the below, all of which are included in the technical scope of the present invention. In the drawings, hatching or a reference sign for a member may be omitted for convenience, and in such a case, the description and other drawings should be referred to. In addition, sizes of various members in the drawings may differ from the actual sizes thereof, since priority is given to understanding the features of the present invention.

Figure 2A:
FIG. 2A shows a cross-sectional view taken along a line A-A of the balloon catheter shown in FIG. 1.
Figure 2B:
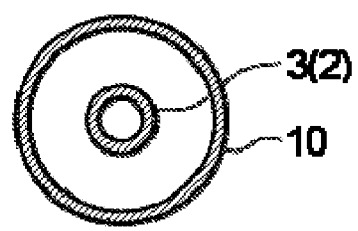
FIG. 2B shows a cross-sectional view taken along a line B-B of the balloon catheter shown in FIG. 1.
Figure 3:
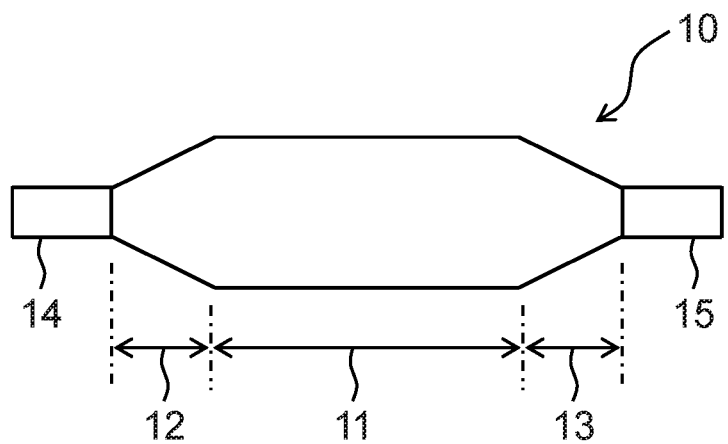
FIG. 3 shows an enlarged view of a balloon provided in the balloon catheter shown in FIG. 1.

The overall configuration of a balloon catheter will be explained with reference to FIGS. 1 to 3. FIG. 1 shows a plan view of a balloon catheter, FIG. 2A and FIG. 2B show cross-sectional views taken along a line A-A and a line B-B of the balloon catheter shown in FIG. 1, respectively, and FIG. 3 shows an enlarged view of a balloon provided in the balloon catheter shown in FIG. 1. FIG. 1 shows a configuration example of an over-the-wire type balloon catheter in which a wire is inserted from a distal end to a proximal end of a shaft. One or more embodiments of the present invention can also be applied to a rapid-exchange type balloon catheter in which a wire is inserted from a distal end to a middle part of a shaft.

The balloon catheter 1 comprises a shaft 2 and a balloon 10 provided on an outside of the shaft 2. The balloon catheter 1 has a proximal side and a distal side, the balloon 10 is provided on the distal side of the shaft 2, and a hub 5 is provided on the proximal side of the shaft 2. In one or more embodiments of the present invention, the proximal side of the balloon catheter means a side toward a user's side, that is an operator's side, with respect to an extending direction of the balloon catheter (particularly the shaft), and the distal side means a direction opposite to the proximal side, that is a direction of a treatment target side. A direction from the proximal side to the distal side of the balloon is referred to as an axial direction.

The balloon catheter 1 is configured such that a pressure fluid is supplied from the hub 5 to an inside of the balloon 10 through the shaft 2, and expansion and contraction of the balloon 10 can be controlled by using an indeflator.

Inside of the shaft 2, a passage for the pressure fluid and a wire insertion path for guiding advancement of the shaft 2 are usually provided. For example, the shaft 2 comprises an inner tube 3 and an outer tube 4, the inner tube 3 functions as the wire insertion path, and a space between the inner tube 3 and the outer tube 4 functions as the passage for the pressure fluid. In this case, the inner tube 3 extends from the distal end of the outer tube 4 and passes through the balloon 10 in the axial direction on the distal side of the shaft 2, and the distal part of the balloon 10 is joined to the inner tube 3 and the proximal part of the balloon 10 is joined to the outer tube 4.

The hub 5 has a fluid injection part 6 connected to the passage of the pressure fluid and a treatment part 7 connected to the wire insertion path. The treatment part 7 can function as an injection port for a drug or the like, or as a suction port for a fluid or the like in a living body cavity, in addition to inserting the wire. In the case of a rapid-exchange type balloon catheter, it may not be necessary to provide the treatment part on the hub.

The balloon 10, the shaft 2 (including the inner tube 3 and the outer tube 4) and the hub 5 can be joined by using a conventionally known joining means such as an adhesive and heat welding. An X-ray opaque marker may be disposed on the shaft 2 at a position where the balloon 10 is located, so that the position of the balloon 10 is able to be confirmed under X-ray fluoroscopy.

As shown in FIG. 3, the balloon 10 has at least a straight tube part 11. In one or more embodiments, the balloon 10 has a proximal taper part 12 connected to a proximal end of the straight tube part 11 and a distal taper part 13 connected to a distal end of the straight tube part 11, and the proximal taper part 12 and the distal taper part 13 are formed so as to decrease in diameter with increasing distance from the straight tube part 11. A cylindrical proximal sleeve 14 is connected to a proximal end of the proximal taper part 12 and a cylindrical distal sleeve 15 is connected to a distal end of the distal taper part 13, and in the catheter shown in FIG. 1, the proximal sleeve 14 is joined to the outer tube 4 of the shaft 2 and the distal sleeve 15 is joined to the inner tube 3 of the shaft 2. An outer diameter and a length in the axial direction of the straight tube part 11 and a taper angle and a length in the axial direction of the taper parts 12, 13 may be appropriately set according to a desired function of the balloon 10. The balloon 10 also can be formed in a substantially cylindrical shape by setting the taper angle of the taper parts 12, 13 to 90° with respect to the axial direction. The balloon 10 is configured so that the parts from the proximal taper part 12 to the distal taper part 13 through the straight tube part 11 are inflated as the pressure fluid is supplied, and in one or more embodiments of the present invention, the inflatable part is regarded as a balloon.

The balloon can be manufactured by molding a resin. For example, the balloon can be manufactured by placing a resin tube, which has been extruded by extrusion molding, in a mold and performing biaxial stretch blow molding. The balloon can be formed into any shape according to the shape of the mold. The balloon can also be manufactured by a known molding method such as dip molding, injection molding, compression molding and the like.

Examples of the resin constituting the balloon include a polyamide resin, a polyester resin, a polyurethane resin, a polyolefin resin, a vinyl chloride resin, a silicone resin, a natural rubber and others. These may be used alone, or two or more of them may be used in combination. In one or more embodiments, a polyamide resin, a polyester resins and a polyurethane resin are preferably used. For these resins, an elastomer resin may be preferably used from the viewpoint of thinning and flexibility of the balloon. For example, among polyamide resins, nylon 12, nylon 11 and the like are mentioned as materials suitable for the balloon, and nylon 12 is suitably used from the viewpoint that it can be molded relatively easily by blow molding. In view of thinning and flexibility of the balloon, polyamide elastomers such as a polyether ester amide elastomer and a polyamide ether elastomer may be used. In one or more embodiments, a polyether ester amide elastomer is preferably used in view of high yield strength and good dimensional stability of the balloon.

The balloon may be configured such that a reinforcing material may be provided on an outer surface of the resin layer formed as described above, in order to improving dimensional stability against expansion pressure. As the reinforcing material, for example, a fiber material can be used, and by disposing a fiber material on the outer surface of the resin layer, a reinforced balloon can be obtained. The reinforcing material may be disposed on the entire outer surface of the resin layer without any gaps or may be disposed only on a part of the outer surface of the resin layer. Examples of the fiber material used as the reinforcing material include a polyarylate fiber, an aramid fiber, an ultrahigh molecular weight polyethylene fiber, a PBO fiber, a carbon fiber and others. These fiber materials may be monofilaments or multifilaments.

The size of the balloon may be appropriately determined according to the size of the treatment site or the like. For example, in the case where the treatment site is a blood vessel, it may be preferable that the length in the axial direction is 5 mm to 300 mm and the outer diameter is 1 mm to 12 mm, and in the case where the treatment site is a digestive tract such as a duodenal papilla, it may be preferable that the length in the axial direction is 10 mm to 100 mm and the outer diameter is 3 mm to 30 mm.

A drug is provided on the outer surface of the balloon 10. The drug provided on the balloon is not particularly limited as long as it is a pharmacologically active substance, and examples of the drug include, for example, a gene therapy drug, a non-gene therapy drug and a pharmaceutically acceptable drug such as a small molecule and a cell. In one or more embodiments, in the case where the balloon catheter is used for a purpose of suppressing restenosis of a blood vessel after treatment in angioplasty, an anti-restenosis agent such as an antiproliferative agent and an immunosuppressive agent can be preferably used as the drug, and specifically, a drug such as paclitaxel, sirolimus (rapamycin), everolimus and zotarolimus can be used. These drugs may be used alone, or two or more of them may be used.

The drug may be held on the balloon as a drug layer or may be held on the balloon in the form of microcapsules or the like. The drug may be held also in the form such that the drug penetrates in the outer surface of the balloon. The drug may contain additives for improving dispersibility, solubility, transferability to a vessel wall, or storage stability of the drug, in addition to the pharmacologically active substance. As the additives, a stabilizer, a binder, a disintegrant, a moisture-proofing agent, a preservative, a dissolution aid and the like are used, and specific examples thereof include lactose, sucrose, maltose, dextrin, xylitol, erythritol, mannitol, ethylenediamine, potassium iodide, urea, polysorbate, dibutylhydroxytoluene, sodium pyrosulfite, ascorbic acid, tocopherol, benzoic acid, paraoxybenzoic acid esters and others.

The drug may be held on the balloon in the state that it is protected by a coating layer to prevent the drug from dissolving or falling off into a blood during delivery to a stenosis part or a lesion part. In one or more embodiments, the coating layer is preferably composed of a water-soluble polymer in view of preventing an initial burst of the drug, and it can be formed from carboxymethylcellulose, hydroxypropylcellulose, methylcellulose, hydroxyethylcellulose, polyvinyl alcohol, alginic acid, pectin, gum arabic, gellan gum, guar gum, xanthan gum, carrageenan, gelatin or the like.

A surface treatment may be applied to the outer surface of the balloon to enhance adhesion of the drug or the coating layer to the balloon surface. Examples of the surface treatment include plasma treatment, laser treatment, ion treatment, ozone treatment, discharge treatment, primer treatment and others.

In order to facilitate transfer of the drug held on the balloon to an inner wall of a blood vessel or the like by lengthening an extension time of the balloon, a perfusion type balloon catheter having a perfusion lumen through which blood or the like can pass through between the proximal side and the distal side of the balloon may be adopted as the balloon catheter.

The balloon catheter according to one or more embodiments of the present invention is formed such that the expansion of the balloon in the radial direction is suppressed when the balloon is pressurized with a relatively high pressure, in order to effectively expand a calcified stenosis part or a hardened lesion part of a blood vessel. Specifically, the balloon is formed such that a change ratio of the outer diameter of the straight tube part, (D28−D24)/D24, is 1.1% or less, provided that the outer diameter of the straight tube part when pressurized at 2.43 MPa (24 atm) is D24 and the outer diameter of the straight tube part when pressurized at 2.84 MPa (28 atm) is D28. The balloon formed in this manner can effectively expand a hard stenosis or lesion part with a high expansion pressure, since the balloon is formed to have a desired outer diameter at relatively high expanding pressure of 24 atm to 28 atm, and expansion of the balloon in the radial direction is suppressed in that pressure range. Therefore, by disposing the drug on the outer surface of such a balloon, it is possible to deliver the drug deeply into a hard stenosis or lesion part to which a drug is usually hard to be delivered. The balloon may be formed such that the outer diameter of the balloon closes to a desired outer diameter even when the expansion pressure is lower than 24 atm (that is, the outer diameter closes to the outer diameter of the balloon at the expansion pressure of 24 atm). In one or more embodiments, the change ratio of the outer diameter, (D28−D24)/D24, is preferably 0.8% or less, more preferably 0.6% or less, and even more preferably 0.4% or less. The lower limit of the change ratio of the outer diameter, (D28−D24)/D24, is not particularly limited, and it may be 0.0% or more. The pressure value at the time of pressurization corresponds to a value of a pressure gauge of a deflator which is a device used to expand the balloon. The same applies to the followings.

In one or more embodiments, the balloon is preferably formed such that expansion of the balloon in the axial direction is also suppressed. In one or more embodiments, the balloon is preferably formed such that a change ratio of a length of the straight tube part in the axial direction, (L28−L24)/L24, is 0.7% or less, provided that the length of the straight tube part in the axial direction when pressurized at 2.43 MPa (24 atm) is L24 and the length of the straight tube part in the axial direction when pressurized at 2.84 MPa (28 atm) is L28. Some drugs held on a drug-eluting balloon catheter that suppresses restenosis of a blood vessel have an adverse effect when it is applied to an inner wall of a normal blood vessel which is not a stenosis part or a lesion part. In the drug-eluting balloon catheters hitherto, expansion in the axial direction could not be suppressed and the drug was applied also to a normal blood vessel, and as a result, new lesions sometimes occurred on a proximal side or a distal side of a lesion though it could prevent restenosis of the lesion. However, by forming the balloon as described above, expansion of the balloon in the axial direction is suppressed when the balloon is pressurized to 24 atm to 28 atm, and it becomes easy to apply the drug to a limited range of a blood vessel wall such as a stenosis part or a lesion part while preventing from applying the drug to an unintended normal blood vessel. Further, by appropriately selecting the balloon which length of the straight tube part matches the length of a stenosis part, a lesion part or the like, it becomes possible to apply more amount of the drug held on the balloon to a targeted stenosis part, a lesion part or the like. In one or more embodiments, the change ratio of the length in the axial direction, (L28−L24)/L24, is more preferably 0.5% or less, and even more preferably 0.3% or less. The lower limit of the change ratio of the length in the axial direction, (L28−L24)/L24, is not particularly limited, and it may be 0.0% or more.

In one or more embodiments, the balloon is preferably formed such that expansion in the axial direction is smaller than that in the radial expansion. In one or more embodiments, it is preferable that the change ratio of the length in an axial direction, (L28−L24)/L24, is smaller than the change ratio of the outer diameter, (D28−D24)/D24. As the balloon is formed in this manner, it is possible to prevent the reduction of the effect of expanding a stenosis part or a lesion part, that is, prevent from escaping pressure that is caused by the balloon expanding in the axial direction when the balloon is pressurized to 24 atm to 28 atm. In one or more embodiments, the change ratio of the length in the axial direction, (L28−L24)/L24, is preferably smaller than the change ratio of the outer diameter, (D28−D24)/D24, by 0.1% or more, more preferably by 0.3% or more, for example.

As a method of forming such a balloon, it may be preferable that a fiber reinforcement layer is formed on a base balloon. In one or more embodiments, the fiber reinforcement layer is preferably formed on the outside of the base balloon and can be formed, for example, by providing a fiber material described above on the outer surface of the base balloon. By forming the fiber material used for the fiber reinforcement layer into a flat shape and disposing it without a gap along a circumferential direction of the balloon, the surface of the balloon can be formed smoothly and the drug is able to be held on the whole outer surface of the balloon. The fiber material may be arranged extending along the axial direction of the balloon, and in this case, expansion in the axial direction can be suppressed. The fiber material of the fiber reinforcement layer may be arranged extending along the circumferential direction of the balloon as well as along the axial direction. In this case, from the view-point of suppressing expansion in the axial direction rather than expansion in the radial direction of the balloon, the fiber material extending along the axial direction is higher in strength and harder to elongate (namely, higher in elastic modulus) than the fiber material extending along the radial direction.

In terms of suppressing the change ratio of the outer diameter or the axial direction when pressurized at a high pressure of 24 atm to 28 atm and easily improving a supply performance of the drug to a blood vessel wall and retention property of the drug during delivery, the balloon may be formed such that a reinforcement part is provided on the outer surface of the base balloon in a linear pattern or a net-like pattern. In one or more embodiments, it is preferable that the drug is provided on the reinforcement part or a part other than the reinforcement part on the outer surface of the balloon. This will be explained below with reference to FIGS. 4 to 8.

Figure 4:
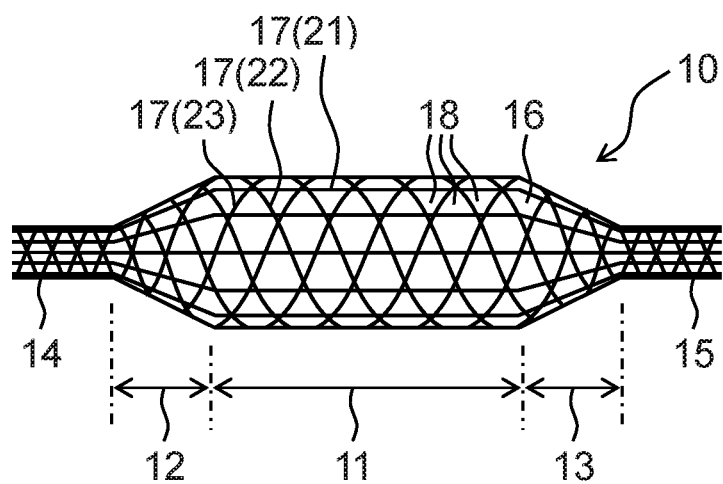
FIG. 4 shows another example of a plan view of a balloon.

FIG. 4 shows a structural example of the balloon in which a reinforcement part is provided on the surface of a base balloon. The balloon 10 comprises a base balloon 16 and a reinforcement part 17 provided on the outer surface of the base balloon 16 in a linear pattern or a net-like pattern and the reinforcement part 17 is formed to protrude on the outer surface of the base balloon 16. In FIG. 4, the reinforcement part is arranged in a net-like pattern. The base balloon 16 defines a fundamental shape of the balloon 10 and is formed in a bag shape having openings on the proximal side and the distal side respectively. The reinforcement part 17 is provided in a linear pattern or a net-like pattern on the outer surface of the base balloon 16, and the reinforcement part 17 is fixed to the outer surface of the base balloon 16 in this pattern. By providing the reinforcement part 17 on the outer surface of the base balloon 16, it is possible to increase the strength of the balloon 10 and suppress the excessive expansion at the time of pressurization. It is also possible to impart a scoring function to the reinforcement part 17 and crack it into a calcified stenosis part to expand it in angioplasty.

The reinforcement part 17 is formed so as to protrude on the outer surface of the balloon 10, that is, protrude outward in the radial direction of the balloon on the outer surface of the balloon 10. A non-reinforcement part 18 is formed at a part other than the reinforcement part 17 on the outer surface of the balloon 10. Therefore, on the outer surface of the balloon 10, the reinforcement part 17 is formed to protrude relative to the non-reinforcement part 18, and the non-reinforcement part 18 is formed to be recessed with respect to the reinforcement part 17. In the balloon 10, the reinforcement part 17 is formed thicker than the non-reinforcement part 18.

The base balloon can be manufactured by molding a resin in the same manner as in the above description concerning the manufacture of the balloon. A method of forming the base balloon and the resin preferably used in one or more embodiments are as described above. The base balloon may be composed of only a resin layer or may comprise a fiber reinforcement layer in addition to the resin layer. In one or more embodiments, the fiber reinforcement layer is preferably formed on the outer surface of the resin layer and can be formed, for example, by providing a fiber material described above on the outer surface of the resin layer.

The reinforcement part may be made of the same material as the base balloon or may be made of a different material from that. In one or more embodiments, the reinforcement part is preferably made of a material which is higher in strength and less stretchable than the base balloon (particularly the resin layer constituting the base balloon). By constituting the reinforcement part in this manner, the reinforcement part can be made to have a scoring function and to enhance dimensional stability at the time of pressurization of the balloon.

The reinforcement part can be formed by, for example, bonding a fiber material to the outer surface of the base balloon. Examples of the fiber material forming the reinforcement part are as described above. In view of increasing strength of the balloon, the fiber material may be preferably higher in strength and harder to stretch (higher in elastic modulus) than the base balloon (particularly the resin layer constituting the base balloon), and the fiber material may have high tensile strength. In the case where the base balloon has the fiber reinforcement layer as described above and the reinforcement part is formed by providing the fiber material on the outer surface of the fiber reinforcement layer, the fiber reinforcement layer is formed to have a uniform height on the outer surface of the base balloon, and a part protruding therefrom is regarded as the reinforcement part.

For example, in the case of the balloon shown in FIG. 4, a plurality of fiber materials 21 arranged parallel to the axial direction and spaced in the circumferential direction of the base balloon and a plurality of fiber materials 22, 23 arranged helically on the base balloon are overlapped to each other without being knitted or are knitted to each other, whereby the reinforcement part can be formed. In the case of overlapping the fiber materials without being knitted, the fiber materials 21, the fiber materials 22(23) and the fiber materials 23(22) may be disposed in this order from the surface of the base balloon 16 over the entire axial length of the base balloon 16; the fiber materials 22(23), the fiber materials 21 and the fiber materials 23(22) may be disposed in this order from that; or the fiber materials 22(23), the fiber materials 23(22) and the fiber materials 21 may be disposed in this order from that. In the case of knitting the fiber materials, the fiber materials 21, 22, 23 may be knitted by regularly exchanging their position on the outer side and the inner side in the radial direction of the balloon. The winding direction of the helically-arranged fiber material 22 is opposite to that of the helically-arranged fiber material 23. The fiber materials 21, 22, 23 may be wound evenly or unevenly. For example, when the fiber materials 21, 22, 23 are formed by gathering a plurality of fibers together, it becomes easy to dispose a large number of fibers in the circumferential direction without using a complicated apparatus, that realizes convenient manufacturing.

In view of suppressing expansion of the balloon in the axial direction, it may be preferable that the elastic modulus of the fiber material 21 extending parallel to the axial direction is higher than the elastic modulus of the fiber materials 22, 23 extending helically in the circumferential direction.

Examples of a method of bonding the fiber material to the base balloon include: a method of coating an adhesive from the outside of the fiber material in a state where the fiber material is placed on the outer surface of the base balloon; a method of applying an adhesive to the base balloon and/or the fiber material and disposing the fiber material on the outer surface of the base balloon; a method of joining the fiber material to the base balloon by thermal bonding; and others. As the adhesive, a resin can also be used.

The number of the fiber materials may be appropriately determined in consideration of the size of the base balloon, the thickness of the fiber material (the height and the line width of the reinforcement part), the strength of the balloon, the retaining amount of the drug, and the like. For example, it may be preferable that a plurality of the fiber materials extending in the axial direction (that is, the reinforcement parts extending linearly in the axial direction) are arranged at intervals in the circumferential direction, and the number of those arranged in the circumferential direction in this case may be preferably 3 to 30. In one or more embodiments, the number of the fiber materials winding helically (that is, the reinforcement parts extending helically) is preferably 3 to 30, and the winding angle of those is in the range of 50° to 80° with respect to the axial direction.

Figure 5A:
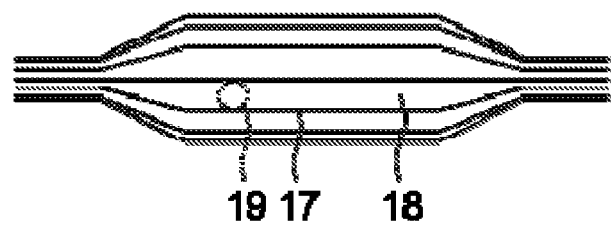
FIGS. 5A to 5C show examples of a plan view of a balloon.
Figure 5B:
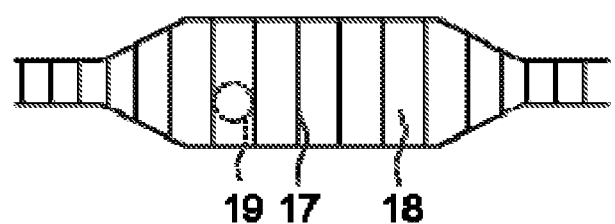
Figure 5C:
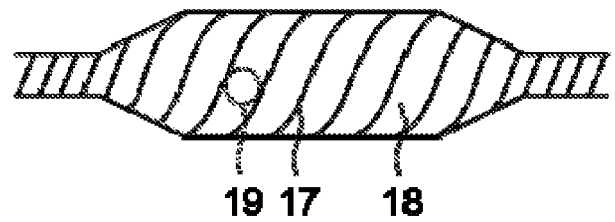

Examples of the embodiment of the reinforcement part 17 arranged in a linear pattern include: an embodiment in which the linear reinforcement part 17 is disposed so as to extend in the axial direction of the balloon (see FIG. 5A); an embodiment in which the linear reinforcement part 17 is disposed so as to extend in the circumferential direction, thereby arranged in a ring shape (see FIG. 5B; an embodiment in which the linear reinforcement part 17 is disposed in a helical pattern (a coil shape) on the outer surface of the base balloon (see FIG. 5C); and the like. In this case, a plurality of the linear reinforcement parts may be provided, but the respective reinforcement parts are arranged so as not to cross each other.

Figure 6A:
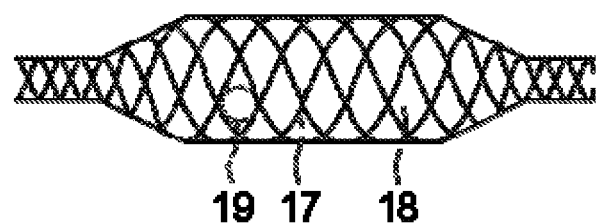
FIGS. 6A and 6B show examples of a plan view of a balloon.
Figure 6B:
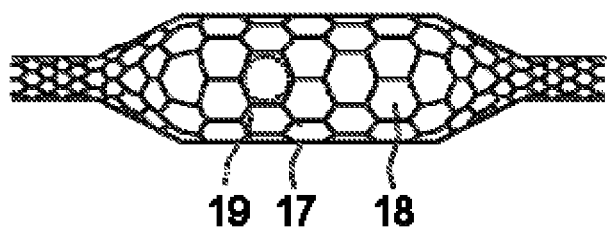

The reinforcement part provided in a net-like pattern is not particularly limited as long as it is arranged so that the linear reinforcement parts intersect with each other, and for example, it can be formed by combining the embodiments of the liner pattern described above. At the intersection of the linear reinforcement parts, the linear reinforcement parts may simply intersect each other (overlapping structure) or a knitted structure may be formed (braided structure). FIG. 4 shows an embodiment in which the reinforcement part is arranged in a net-like pattern that is formed by combining a axially-extending linear pattern, a right-handed helical pattern and a left-handed helical pattern. FIG. 6A shows an embodiment in which the reinforcement part is arranged in a net-like pattern that is formed by combining a right-handed helical pattern and a left-handed helical pattern. The reinforcement part may be provided in a lattice pattern such as a triangular lattice pattern or a hexagonal lattice pattern as the net-like pattern. FIG. 6B shows an embodiment in which the reinforcement parts are arranged in a hexagonal lattice pattern.

A height and a line width of the reinforcement part may be appropriately determined according to a desired performance of the balloon. The reinforcement parts may be provided so that all of them have the same height to each other or may be provided so that some of them have a different height from others of them. The reinforcement parts may be provided so that all of them have the same line width to each other or may be provided so that some of them have a different line width from others of them. In view of suppressing expansion of the balloon in the axial direction, it may be preferable that the line width of the reinforcement part extending parallel to the axial direction is larger than the line width of the reinforcement part extending in the circumferential direction. In one or more embodiments, the height of the reinforcement part is preferably, for example, 0.01 mm or more, more preferably 0.1 mm or more, and is preferably 0.5 mm or less. The height of the reinforcement part means a height projecting from the outer surface of the balloon and can be obtained by measuring a height from the non-reinforcement part. In the case where the reinforcement part is formed from the fiber material, the thickness of the fiber material may be regarded as the height of the reinforcement part. In one or more embodiments, the line width of the reinforcement part is preferably, for example, 0.02 mm or more, more preferably 0.1 mm or more, and is preferably 0.3 mm or less. For example, the line width of the reinforcement part is obtained by measuring a width at a half height of the reinforcement part (that is, a width of the reinforcement part at which the height of that is half) or in the case where the reinforcement part is formed from the fiber material, the width (thickness) of the fiber material may be regarded as the line width of the reinforcement part. The height and the line width of the reinforcement part can be obtained by observing a cross section of the balloon.

A ratio of the reinforcement part on the outer surface of the balloon, that is, a ratio of an area occupied by the reinforcement part on the outer surface of the balloon, may be appropriately set according to a desired performance of the balloon. For example, the ratio of the area of the reinforcement part in the straight tube part of the balloon may be preferably 30% or more, more preferably 50% or more, in view of suppressing excessive expansion and enhancing a shape retention property of the balloon when the balloon is pressurized. Meanwhile, the upper limit of the ratio of the area of the reinforcement part in the straight tube part of the balloon is not particularly limited, and may be, for example, 80% or less, or 60% or less. The ratio of the area of the reinforcement part on the outer surface of the balloon can determined as follows that: a boundary between the reinforcement part and the non-reinforcement part is defined at a half height of the reinforcement part, a portion higher than the boundary is regarded as the reinforcement part, and the area of the reinforcement part can be obtained therefrom. In the case where the reinforcement part is formed from the fiber material, an installation area of the fiber material (a projected area on the surface of the base balloon) may be regarded as the area of the reinforcement part.

The height, the line width and the ratio of the area of the reinforcement part described above are obtained by cutting or developing the balloon and measuring the balloon in a non-pressurized state. Various values described below also mean values in a non-pressurized state of the balloon, unless otherwise specified.

In the case where the reinforcement part is provided on the outer surface of the balloon, the drug may be preferably held on the reinforcement part, for example. When the drug is held on the reinforcement part of the balloon, the drug can be delivered deeply into a stenosis part or a lesion part also by a scoring function of the reinforcement part.

In view of enhancing the scoring function of the reinforcement part and facilitating delivery of the drug deeply into a stenosis part or a lesion part, it may be preferable that the balloon is provided with the reinforcement part with a height of 0.2 mm or more and 0.5 mm or less. When the reinforcement part of such a height is provided on the outer surface of the balloon, the reinforcement part bites into a stenosis part or a lesion part so that the drug is easily delivered deeply into the stenosis part or the lesion part. In addition, since the reinforcement part can suppress excessive expansion at the time of balloon pressurization, it is also possible to deliver the drug deeply into a calcified stenosis part in angioplasty. The height of the reinforcement part described here means a maximum height of the reinforcement part, and the balloon may be provided with the reinforcement part having a height lower than this.

In the case where the drug is held on the reinforcement part, the reinforcement part may be preferably provided such that its protruding state on the outer surface of the balloon stands out, and in one or more embodiments, it is preferably provided with a certain interval from the adjacent reinforcement part. In view of this point, a part other than the reinforcement part may be preferably formed on the outer surface of the balloon so as to have a size including a circular shape of at least a diameter of 0.5 mm (the diameter may be more preferably 0.8 mm, and even more preferably 1.0 mm). By providing the reinforcement part in this manner, it becomes easy to enhance the scoring function of the reinforcement part and deliver the drug deeply into a stenosis part or a lesion part. Meanwhile, in view of ensuring the amount of the drug to be delivered to a stenosis part or a lesion part, the part other than the reinforcement part may be preferably formed on the outer surface of the balloon so as to have a size not including a circular shape of a diameter of 1.5 mm (the diameter may be more preferably 1.3 mm, and even more preferably 1.1 mm). For example, in the balloons shown in FIG. 5A to FIG. 5C and FIG. 6A to FIG. 6B, the diameter of a inscribed circle 19 contacting a plurality of adjacent reinforcement parts 17 may be preferably 0.5 mm or more, and preferably less than 1.5 mm. The inscribed circle 19 is defined so as to have the largest diameter at the area surrounded by the reinforcement parts 17 or at the area sandwiched therebetween.

In one or more embodiments, the size of the part other than the reinforcement part described above is preferably determined for the reinforcement part having a height of 0.2 mm or more and 0.5 mm or less. In one or more embodiments, on the outer surface of the balloon, it is preferable that a part other than the reinforcement part having a height of 0.2 mm or more and 0.5 mm or less is formed in a size including a circular shape of at least a diameter of 0.5 mm, and it is preferable that it is formed in a size not including a circular shape of a diameter of 1.5 mm. In one or more embodiments, a preferable range of the height of the reinforcement part and a preferable range of the size of the part other than the reinforcement part are as described above. By providing the reinforcement part in this manner, it becomes easy to increase the scoring function of the balloon and deliver more amount of the drug deeply into a stenosis part or a lesion part.

In the case where the drug is provided on the reinforcement part, it may be preferable that the reinforcement part protrudes outward in the radial direction of the balloon relative to the part other than the reinforcement part on the outer surface of the balloon even when pressurized at 2.63 MPa (26 atm). The reinforcement part is formed so as to protrude outward on the outer surface of the balloon when the balloon is not pressurized; and furthermore, as the reinforcement part is formed so as to protrude outward on the outer surface of the balloon even at the time of pressurization of 26 atm, the reinforcement part is able to bite into a calcified stenosis part when the balloon is pressurized to a high pressure of 26 atm. Therefore, it becomes easy to deliver the drug deeply into a calcified stenosis part.

In the case where the reinforcement part is provided on the outer surface of the balloon, the drug may be held on a part other than the reinforcement part on the outer surface of the balloon. In this case, the drug is held on at least the non-reinforcement part on the outer surface of the balloon. Since the non-reinforcement part of the balloon is recessed with respect to the reinforcement part, when the drug is held on the non-reinforcement part, dissolving or falling of the drug during delivery can be suppressed. As the balloon is pressurized and expanded, the interval between the adjacent reinforcement parts is widened or the non-reinforcement part is pressed from the inside of the balloon, whereby the drug held on the non-reinforcement part can be transferred to a stenosis part or a lesion part. In the case where the reinforcement part has a scoring function, it is also possible to crack a stenosis part or a lesion part by the reinforcement part and deliver the drug deeply further into the stenosis part or the lesion part.

In the case where the drug is held on the part other than the reinforcement part, it may be preferable that the balloon is provided with the reinforcement part with a height of 0.1 mm or more and 0.5 mm or less, in view of suppressing dissolution or falling off of the drug during delivery. By forming the reinforcement part in this manner, a scoring function by the reinforcement part can be expected, and it becomes possible to crack a stenosis part or a lesion part when the balloon is expanded, thereby delivering the drug deeply into the stenosis part or the lesion part. Meanwhile, as the height of the reinforcement part is too high, the drug tends to remain on the outer surface of the balloon when the balloon is expanded, so the height of the reinforcement part may be preferably 0.5 mm or less. The height of the reinforcement part described here means a maximum height of the reinforcement part, and the balloon may be provided with another reinforcement part having a height lower than this.

In the case where the drug is held on the part other than the reinforcement part, the part other than the reinforcement part may be preferably formed on the outer surface of the balloon so as to have a size not including a circular shape of a diameter of 1.5 mm (the diameter may be more preferably 1.3 mm, and even more preferably 1.1 mm), in view of suppressing dissolution or falling off of the drug during delivery. Meanwhile, in view of ensuring the retaining amount of the drug, the part other than the reinforcement part may be preferably formed on the outer surface of the balloon so as to have a size including a circular shape of at least a diameter of 0.5 mm (the diameter may be more preferably 0.8 mm, and even more preferably 1.0 mm). By forming the balloon in this manner, the interval between the adjacent reinforcement parts is easily widened or the non-reinforcement part is easily pressed from the inside of the balloon as the balloon is pressurized and expanded, so that the drug is easily released.

In the case where the drug is held on the part other than the reinforcement part, the reinforcement part may be preferably arranged in a net-like pattern, in view of suppressing dissolution or falling off of the drug during delivery. In one or more embodiments, the part other than the reinforcement part is preferably provided on the outer surface of the balloon with an area of 8.0 mm$^2$ or less, and more preferably 7.5 mm$^2$ or less. Meanwhile, in view of ensuring the retaining amount of the drug, the part other than the reinforcement part may be provided with an area of 0.1 mm$^2$ or more, and more preferably 0.4 mm$^2$ or more. By forming the balloon in this manner, the drug held on the part other than the reinforcement part is easily released as the balloon is pressurized and expanded. The area of the part other than the reinforcement part described here means an area of an individual part of the parts other than the reinforcement part.

In the case where the reinforcement part is disposed in a net-like pattern, the reinforcement part may be preferably disposed in a net-like pattern having a polygonal shape of pentagonal or more. By disposing the reinforcement part in this manner, the drug retained in the vicinity of the intersection (nodal point) of the net-like pattern on the outer surface of the balloon also hardly remains on the balloon when the balloon is expanded, so that it becomes easy to transfer more amount of the drug to a stenosis part or a lesion part.

In one or more embodiments, the size and the shape of the part other than the reinforcement part described above is preferably determined for the reinforcement part having a height of 0.1 mm or more and 0.5 mm or less. In one or more embodiments, on the outer surface of the balloon, it is preferable that a part other than the reinforcement part having a height of 0.1 mm or more and 0.5 mm or less is formed in a size not including a circular shape of a diameter of 1.5 mm, and it is preferable that it is formed in a size including a circular shape of a diameter of 0.5 mm. In the case where the reinforcement part having a height of 0.1 mm or more and 0.5 mm or less is provided in a net-like pattern, the part other than the reinforcement part may be preferably provided with an area of 8.0 mm$^2$ or less and may be preferably provided with an area of 0.1 mm$^2$ or more. In one or more embodiments, it is also preferable that the reinforcement part having a height of 0.1 mm or more and 0.5 mm or less is disposed in a net-like pattern having a polygonal shape of pentagonal or more. In one or more embodiments, a preferable range of the height of the reinforcement part and a preferable range of the size of the part other than the reinforcement part are as described above.

In the case where the drug is held on the part other than the reinforcement part, the part other than the reinforcement part on the outer surface of the balloon may be preferably formed to bulge outward in the radial direction of the balloon when the balloon is pressurized. In one or more embodiments, it is preferable that the balloon is formed such that the part other than the reinforcement part on the outer surface of the balloon is formed to bulge outward in the radial direction of the balloon when pressurized at 2.63 MPa (26 atm). By forming the balloon in this manner, the drug retained in the part other than the reinforcement part on the outer surface of the balloon is easily released as the balloon is pressurized and expanded at a stenosis part or a lesion part, whereby the drug can be effectively transferred to the stenosis part or the lesion part.

The degree of bulging of the part other than the reinforcement part on the outer surface of the balloon can be expressed by the height $H_a$ of the reinforcement part on the outer surface of the balloon and the height $H_b$ of the part other than the reinforcement part. The degree of bulging of the part other than the reinforcement part may be determined by the difference ($\Delta H = H_a - H_b$) between the height $H_a$ of the reinforcement part and the height $H_b$ of the part other than the reinforcement part as an index, and $\Delta H_{26}$ at the pressurization of 2.63 MPa (26 atm) may be preferably smaller than $\Delta H_2$ at the pressurization of 0.20 MPa (2 atm). In one or more embodiments, the part other than the reinforcement part is preferably formed so as not to bulge to the height of the reinforcement part when pressurized at 2.63 MPa (26 atm), in view of suppressing expansion of the balloon in the radial direction at 24 atm to 28 atm.

In one or more embodiments, it is also preferable that the balloon is formed so that the area of the part other than the reinforcement part increases at the time of pressurization. As the balloon is formed in this manner, a gap is likely to be formed between the drug held on the part other than the reinforcement part and the reinforcement part when the balloon is pressurized, and the drug held on the balloon is easily released. For example, the balloon may be preferably formed so that the area of the part other than the reinforcement part in the straight tube part of the balloon at pressurization of 2.63 MPa (26 atm) is wider than that at pressurization of 0.20 MPa (2 atm).

The extent of bulging and extensibility of the part other than the reinforcement part on the outer surface of the balloon can be adjusted by appropriately selecting the material and thickness of the base balloon, and the material, thickness and the installation pattern of the reinforcement part.

The reinforcement part may be composed of a main reinforcement part and an auxiliary reinforcement part having a height lower than the main reinforcement part. For example, in the case where the drug is provided on the reinforcement part, it may be preferable that a main reinforcement part having a height of 0.2 mm or more and 0.5 mm or less and an auxiliary reinforcement part having a height of 0.01 mm or more and less than 0.2 mm are provided on the outer surface of the balloon as the reinforcement part. In one or more embodiments, it is preferable that the drug is held on at least the main reinforcement part. In this case, the main reinforcement part can contribute to enhance the scoring function and deliver the drug deeply into a stenosis part or a lesion part, and the auxiliary reinforcement part can contribute to enhance the pressure resistance and shape retention of the balloon. The height of the auxiliary reinforcement part may be more preferably 0.02 mm or more, and more preferably 0.1 mm or less.

In the case where the drug is provided on the part other than the reinforcement part, it may be preferable that a main reinforcement part having a height of 0.1 mm or more and 0.5 mm or less and an auxiliary reinforcement part having a height of 0.01 mm or more and less than 0.1 mm are provided on the outer surface of the balloon as the reinforcement part. In one or more embodiments, it is preferable that the drug is held on the part other than the main reinforcement part on the outer surface of the balloon, and the drug may be held on the auxiliary reinforcement part. The main reinforcement part can contributes to suppress dissolution or falling off of the drug during delivery and the auxiliary reinforcement part can contributes to enhance the pressure resistance and shape retention of the balloon. In one or more embodiments, the height of the auxiliary reinforcement part is more preferably 0.02 mm or more, and more preferably 0.08 mm or less.

Figure 7:
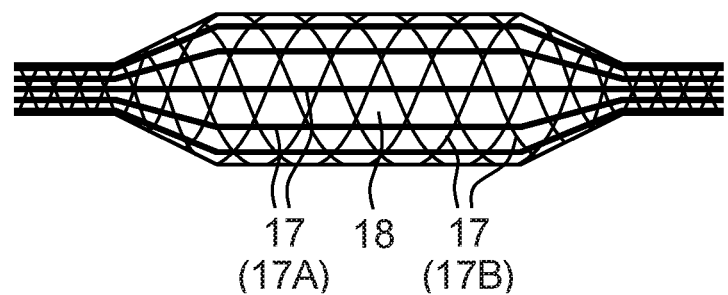
FIG. 7 shows another example of a plan view of a balloon.
Figure 8:
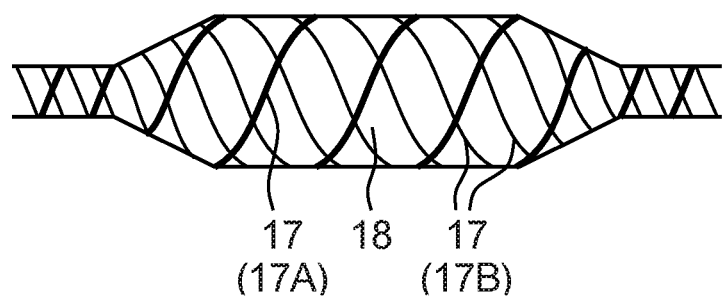
FIG. 8 shows another example of a plan view of a balloon.

FIGS. 7 and 8 show examples of the balloons provided with the main reinforcement part and the auxiliary reinforcement part as the reinforcement parts. In the balloon shown in FIG. 7, the reinforcement part 17 extending in the axial direction of the balloon is provided as a main reinforcement part 17A and the reinforcement part 17 extending helically in the circumferential direction of the balloon is provided as an auxiliary reinforcement part 17B in the balloon shown in FIG. 4. In the balloon shown in FIG. 8, among reinforcement parts 17 extending in helically in one direction or the other direction of the circumference of the balloon, the reinforcement part 17 extending helically in one direction is provided as a main reinforcement part 17A and the reinforcement part 17 extending helically in the other direction is provided as an auxiliary reinforcement part 17B.

In the case where the drug is provided on the reinforcement part, the part other than the main reinforcement part may be preferably formed on the outer surface of the balloon so as to have a size including a circular shape of at least a diameter of 0.5 mm (the diameter may be more preferably 0.8 mm, and even more preferably 1 mm). In one or more embodiments, the part other than the main reinforcement part is preferably formed so as to have a size not including a circular shape of a diameter of 1.5 mm (the diameter may be more preferably 1.3 mm, and even more preferably 1.1 mm). Meanwhile, the arrangement of the auxiliary reinforcement part is not particularly limited, and the auxiliary reinforcement part may be provided at a higher density than the main reinforcement part, may be provided at a lower density than that, or may be provided at the same density as that. In view of enhancing the shape retention of the balloon while securing the scoring function and the drug supply performance by the main reinforcement part, the auxiliary reinforcement part may be preferably provided so that the ratio of the area of the auxiliary reinforcement part is larger than that of the main reinforcement part.

In the case where the drug is provided on the part other than the reinforcement part, the part other than the main reinforcement part may be preferably formed on the outer surface of the balloon so as to have a size not including a circular shape of a diameter of 1.5 mm (the diameter may be more preferably 1.3 mm, and even more preferably 1.1 mm). In the case where the reinforcement part is provided in a net-like pattern, the part other than the main reinforcement part may be preferably provided with an area of 8.0 mm$^2$ or less (the area may be more preferably 7.5 mm$^2$ or less) and 0.1 mm$^2$ or more (the area may be more preferably 0.4 mm$^2$ or more). In one or more embodiments, it is also preferable that the main reinforcement part is disposed in a net-like pattern having a polygonal shape of pentagonal or more. Meanwhile, the arrangement of the auxiliary reinforcement part is not particularly limited, and the auxiliary reinforcement part may be provided at a higher density than the main reinforcement part, may be provided at a lower density than that, or may be provided at the same density as that. In view of securing the retaining amount of drug on the balloon and enhancing the shape retention property of the balloon, the auxiliary reinforcement part may be preferably provided so that the ratio of the area of the auxiliary reinforcement part is larger than that of the main reinforcement part.

In one or more embodiments, it is preferable that at least a part of the reinforcement part is provided so as to extend in the axial direction of the balloon. In order to securely transfer the drug held on the outer surface of the balloon to a vessel wall or the like, it is desirable to expand the balloon in the blood vessel for a certain period of time; however, since expansion of the balloon causes obstruction of a blood flow, the expansion time of the balloon is restricted in reality. However, when at least a part of the reinforcement part is provided so as to extend in the axial direction of the balloon, a space extending in the axial direction of the balloon is likely to be formed between the balloon and a blood vessel wall when the balloon is expanded. That is, between the balloon and a blood vessel wall, a space is likely to be formed between adjacent axially extending portions of the reinforcement part. Therefore, it becomes possible to prevent a blood flow from being completely stopped when the balloon is expanded, so that the balloon can be expanded for a long time. In addition, expansion of the balloon in the axial direction at the time of pressurization tends to be suppressed.

In one or more embodiments, a part of the reinforcement part is provided so as to extend in the axial direction of the balloon, and the other part of that is provided so as to extend helically in the circumferential direction of the balloon. In this case, expansion of the balloon in the radial direction at the time of pressurization can also tends to be suppressed.

In the case where the main reinforcement part and the auxiliary reinforcement part are provided on the balloon, it may be preferable that the main reinforcement part 17A is provided so as to extend in the axial direction of the balloon and the auxiliary reinforcement part 17B is provided so as to extend in the circumferential direction of the balloon, as shown in FIG. 7. The part extending in the circumferential direction may extend helically in the circumferential direction or may extend in the circumferential direction so as to form a ring. In this case, provided that a portion of the reinforcement part extending in the axial direction of the balloon is referred to as an axially extending portion and a portion of the reinforcement part extending in the circumferential direction of the balloon is referred to as a circumferentially extending portion, the main reinforcement part may be preferably provided only in the axially extending portion. A part of the axially extending portion may be composed of the auxiliary reinforcement part. In one or more embodiments, the circumferentially extending portion is preferably composed only of the auxiliary reinforcement part. When the main reinforcement part and the auxiliary reinforcement part are provided in this manner, a space is easily formed between the balloon and a blood vessel wall between the adjacent axially extending portions of the reinforcement part, and therefore, a blood flow can be maintained when the balloon is expanded and the time for balloon expansion can be taken longer.

In the case where the main reinforcement part and the auxiliary reinforcement part are provided on the balloon, it may also be preferable that the main reinforcement part 17A is provided so as to extend helically in one direction in the circumferential direction of the balloon and the auxiliary reinforcement part 17B is provided so as to extend helically in an opposite direction to the main reinforcement part in the circumferential direction of the balloon, as shown in FIG. 8. In this case, provided that a portion of the reinforcement part extending helically in one direction is referred to as a first helically extending portion and a portion of the reinforcement part extending helically in the other direction is referred to as a second helically extending portion, the main reinforcement part may be preferably provided only in the first helically extending portion, and a part of the first helically extending portion may be composed of the auxiliary reinforcement part. In one or more embodiments, the second helically extending portion is preferably composed only of the auxiliary reinforcement part. On the balloon configured in this manner, an axially extending portion may be further provided as the reinforcement part: but in one or more embodiments, it is preferable that the axially extending portion is composed only of the auxiliary reinforcement part. When the main reinforcement part and the auxiliary reinforcement part are provided in this manner, the main reinforcement part bites into a stenosis part or a lesion part so as to be oblique to the extending direction of a blood vessel and it becomes easy to expand the blood vessel to the entire circumferential direction. Therefore, the scoring function by the reinforcement part can be exerted more effectively, and when the balloon is expanded, a stenosis part or a lesion part can be expanded and the drug held on the balloon is easily delivered deeply into the stenosis part or the lesion part.

This application claims priority to Japanese Patent Application No. 2016-132844, filed on Jul. 4, 2016. All of the contents of the Japanese Patent Application No. 2016-132844, filed on Jul. 4, 2016, are incorporated by reference herein.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

REFERENCE SIGNS LIST

1: a balloon catheter
2: a shaft
3: an inner tube
4: an outer tube
5: a hub
10: a balloon
11: a straight tube part
12: a proximal taper part
13: a distal taper part
16: a base balloon
17, 17A, 17B: a reinforcement part
18: a non-reinforcement part

What is claimed is:

1. A balloon catheter comprising:
a shaft; and
a balloon provided outside the shaft,
wherein a drug is provided on an outer surface of the balloon,
wherein the balloon has at least a straight tube part, and
wherein a change ratio of an outer diameter of the straight tube part, $(D28-D24)/D24$, is 1.1% or less, provided that $D24$ is the outer diameter of the straight tube part when an internal pressure of 2.43 MPa (24 atm) is applied and $D28$ is the outer diameter of the straight tube part when an internal pressure of 2.84 MPa (28 atm) is applied.

2. The balloon catheter according to claim 1, wherein
a change ratio of a length of the straight tube part in an axial direction, $(L28-L24)/L24$, is 0.7% or less, provided that $L24$ is the length of the straight tube part in the axial direction when an internal pressure of 2.43 MPa (24 atm) is applied and $L28$ is the length of the straight tube part in the axial direction when an internal pressure of 2.84 MPa (28 atm) is applied.

3. The balloon catheter according to claim 1, wherein
a change ratio of a length of the straight tube part in an axial direction, $(L28-L24)/L24$, is smaller than the change ratio of the outer diameter of the straight tube part, $(D28-D24)/D24$, provided that $L24$ is the length of the straight tube part in the axial direction when an internal pressure of 2.43 MPa (24 atm) is applied and $L28$ is the length of the straight tube part in the axial direction when an internal pressure of 2.84 MPa (28 atm) is applied.

4. The balloon catheter according to claim 1, wherein the balloon comprises:
a base balloon; and
a reinforcement part, wherein the reinforcement part is provided on an outer surface of the base balloon in a linear pattern or a net-like pattern and protrudes from the outer surface of the balloon, and wherein the drug is provided on the reinforcement part.

5. The balloon catheter according to claim 4, wherein the reinforcement part has a height of 0.2 to 0.5 mm.

6. The balloon catheter according to claim 4, wherein the reinforcement part protrudes outward in a radial direction of the balloon relative to the outer surface of the balloon when an internal pressure of 2.63 MPa (26 atm) is applied.

7. The balloon catheter according to claim 4, wherein at least a part of the reinforcement part extends in an axial direction of the balloon.

8. The balloon catheter according to claim 4, wherein the reinforcement part is a fiber material bonded to the outer surface of the base balloon.

9. The balloon catheter according to claim 1, wherein the balloon comprises:
a base balloon; and
a reinforcement part, wherein the reinforcement part is provided on an outer surface of the base balloon in a linear pattern or a net-like pattern and protrudes from the outer surface of the balloon, and wherein the drug is provided on a part of the outer surface of the balloon other than the reinforcement part.

10. The balloon catheter according to claim 9, wherein the reinforcement part has a height of 0.1 to 0.5 mm.

11. The balloon catheter according to claim 9, wherein the part other than the reinforcement part on the outer surface of the balloon is formed to bulge outward in a radial direction of the balloon when an internal pressure of 2.63 MPa (26 atm) is applied.

12. The balloon catheter according to claim 9, wherein at least a part of the reinforcement part extends in an axial direction of the balloon.

13. The balloon catheter according to claim 9, wherein the reinforcement part is a fiber material bonded to the outer surface of the base balloon.

14. The balloon catheter according to claim 1, wherein the drug is an antiproliferative agent or an immunosuppressive agent.

\* \* \* \* \*